United States Patent
Lee et al.

(10) Patent No.: US 10,951,068 B2
(45) Date of Patent: Mar. 16, 2021

(54) APPARATUS AND METHOD WITH WIRELESS POWER TRANSMISSION

(71) Applicant: Samsung Electronics Co., Ltd., Suwon-si (KR)

(72) Inventors: Jaechun Lee, Seoul (KR); Sang Joon Kim, Hwaseong-si (KR); Hankyu Lee, Suwon-si (KR); Seungchul Jung, Suwon-si (KR); Yeunhee Huh, Namyangju-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 16/678,351

(22) Filed: Nov. 8, 2019

(65) Prior Publication Data
US 2020/0366133 A1    Nov. 19, 2020

(30) Foreign Application Priority Data
May 14, 2019    (KR) .................. 10-2019-0056221

(51) Int. Cl.
*H02J 50/12*     (2016.01)
*H02J 50/90*     (2016.01)
*H02J 50/50*     (2016.01)
*H02J 50/80*     (2016.01)
*H02J 7/02*      (2016.01)

(52) U.S. Cl.
CPC ............. *H02J 50/12* (2016.02); *H02J 50/50* (2016.02); *H02J 50/80* (2016.02); *H02J 50/90* (2016.02); *A61B 2560/0219* (2013.01); *H02J 7/025* (2013.01)

(58) Field of Classification Search
CPC .... H02J 7/02; H02J 50/12; H02J 50/80; H02J 50/90; H02J 50/50; H02J 7/025; A61B 2560/0219
See application file for complete search history.

(56) References Cited

U.S. PATENT DOCUMENTS

| | | |
|---|---|---|
| 8,587,155 B2 | 11/2013 | Giler et al. |
| 2011/0133569 A1 | 6/2011 | Cheon et al. |
| 2011/0316349 A1 | 12/2011 | Hashiguchi et al. |
| 2012/0032522 A1 | 2/2012 | Schatz et al. |
| 2013/0249306 A1 | 9/2013 | Kim et al. |
| 2014/0152119 A1 | 6/2014 | Endo et al. |
| 2015/0255990 A1 | 9/2015 | Masaoka |
| 2015/0333801 A1 | 11/2015 | Hosotani |

(Continued)

OTHER PUBLICATIONS

Extended European Search Report dated Sep. 9, 2020 in counterpart European Application No. 20170096.0 (8 pages in English).

*Primary Examiner* — Robert L Deberadinis
(74) *Attorney, Agent, or Firm* — NSIP Law

(57) ABSTRACT

A wireless power transmission system includes: a wireless power transmission apparatus including: a transmission coil configured to form mutual coupling with an auxiliary coil disposed outside of a living body; and a controller configured to control a supply of power by a power source to the transmission coil to wirelessly transmit the power from the transmission coil, using the auxiliary coil, to a wireless power reception apparatus disposed inside the living body through the mutual coupling, wherein a distance between the transmission coil and the auxiliary coil is adjustable.

22 Claims, 12 Drawing Sheets

(56) References Cited

U.S. PATENT DOCUMENTS

| | | | |
|---|---|---|---|
| 2016/0308403 A1* | 10/2016 | Bluvshtein | H02J 50/12 |
| 2017/0271919 A1 | 9/2017 | Von Novak, III et al. | |
| 2017/0272123 A1 | 9/2017 | Zhu et al. | |
| 2018/0159382 A1 | 6/2018 | Lin et al. | |

* cited by examiner

APPARATUS AND METHOD WITH WIRELESS POWER TRANSMISSION

CROSS-REFERENCE TO RELATED APPLICATIONS

This application claims the benefit under 35 USC § 119(a) of Korean Patent Application No. 10-2019-0056221 filed on May 14, 2019 in the Korean Intellectual Property Office, the entire disclosure of which is incorporated herein by reference for all purposes.

BACKGROUND

1. Field

The following description relates to apparatuses and methods with wireless power transmission.

2. Description of Related Art

Wireless power may refer to energy that is transmitted from a wireless power transmission apparatus to a wireless power reception apparatus through magnetic coupling. A wireless power charging system may include a source device configured to wirelessly transmit power, and a target device configured to wirelessly receive power. The source device may be referred to as a wireless power transmission apparatus, and the target device may be referred to as a wireless power reception apparatus.

The source device may include a source resonator, and the target device may include a target resonator. Magnetic coupling or resonance coupling may occur between the source resonator and the target resonator.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a wireless power transmission system includes: a wireless power transmission apparatus including: a transmission coil configured to form mutual coupling with an auxiliary coil disposed outside of a living body; and a controller configured to control a supply of power by a power source to the transmission coil to wirelessly transmit the power from the transmission coil, using the auxiliary coil, to a wireless power reception apparatus disposed inside the living body through the mutual coupling, wherein a distance between the transmission coil and the auxiliary coil is adjustable.

The transmission coil may have a structure with a weakly-coupled coupling coefficient less than a threshold value with respect to a reception coil of the wireless power reception apparatus.

A size of the transmission coil may be greater than a size of a reception coil of the wireless power reception apparatus.

The controller may be configured to transmit the power from the power source to the transmission coil, in response to a power transmission input being received from a user.

The system may further include: a connector configured to: connect the wireless power transmission apparatus and the auxiliary coil; and adjust the distance between the transmission coil and the auxiliary coil by adjusting a distance between the wireless power transmission apparatus and the auxiliary coil.

The connector may include: a first housing having one surface configured to be attach to the wireless power transmission apparatus; and a second housing rotatably connected to the first housing and configured to rotate such that a distance between one surface of the second housing and the one surface of the first housing changes, wherein the auxiliary coil is disposed parallel with the one surface of the second housing.

The second housing may include a coil supporting member supporting the auxiliary coil and rotatably connected to at least one of the second housing and the auxiliary coil, and configured to rotate such that a distance between the one surface of the second housing and the auxiliary coil changes.

The system may further include: an auxiliary coil module including the auxiliary coil and configured to support the auxiliary coil spaced by a predetermined distance apart from the wireless power transmission apparatus, wherein the auxiliary coil module is replaceable with another auxiliary coil module with a structure including a differently sized auxiliary coil disposed at a different distance from the wireless power transmission apparatus than the distance between the transmission coil and the auxiliary coil.

The wireless power transmission apparatus may include an input/output (I/O) component configured to output either one or both of a replacement indication and a maintenance indication of the auxiliary coil module, in response to the auxiliary coil module being replaced with a new auxiliary coil module, and the controller may be configured to determine whether to replace the new auxiliary coil module based on whether an impedance of the transmission coil reaches a target impedance.

The auxiliary coil may be attached to a surface of the living body.

The auxiliary coil may be replaceable with a differently sized auxiliary coil.

The system may further include: a communicator configured to receive power information related to power of the auxiliary coil from an auxiliary coil module including the auxiliary coil.

The power information may include information of any one or any combination of any two or more of a voltage, a current, and a magnetic field of the auxiliary coil.

Based on the received power information, the controller may be configured to determine either one or both of whether the distance between the transmission coil and the auxiliary coil is to be adjusted, and whether the auxiliary coil is to be replaced with a differently sized auxiliary coil.

The controller may be configured to output guidance information indicating instructions to either change or maintain the distance between the transmission coil and the auxiliary coil based on the power information.

The communicator may be configured to collect the power information from the auxiliary coil module at a plurality of distances between the wireless power transmission apparatus and the auxiliary coil, in response to the wireless power transmission apparatus moving in one direction with respect to the auxiliary coil, and the controller may be configured to determine a distance among the plurality of distances at which a maximum magnitude of the collected power information is sensed.

The system may further include: an input/output (I/O) component configured to output either one or both of an indication to a user that the wireless power transmission apparatus is to be moved in the one direction and an indication to the user that the wireless power transmission apparatus is to be held at the distance at which the maximum magnitude is sensed.

The system may further include: a communicator configured to transmit, to an auxiliary coil module including auxiliary coils of a plurality of sizes including the auxiliary coil, a signal to activate one of the auxiliary coils.

The controller may be configured to select the one of the auxiliary coils in the auxiliary coil module based on power information received from the auxiliary coil module, and for the transmitting of the signal, the communicator may be configured to transmit the signal to activate the selected auxiliary coil.

The communicator may be configured to transmit signals to sequentially activate the auxiliary coils to the auxiliary coil module, and sequentially receive respective power information corresponding to an activated one of the auxiliary coils sensed by the auxiliary coil module, and the controller may be configured to select, as the one of the auxiliary coils to which the signal to activate is to be transmitted, auxiliary coil of the auxiliary coils corresponding to power information having a maximum magnitude among the sequentially received power information.

The controller may be configured to select, as the one of the auxiliary coils to which the signal to activate is to be transmitted, an auxiliary coil of the auxiliary coils corresponding to a predetermined distance to, and a predetermined size of, a reception coil included in the wireless power reception apparatus.

In another general aspect, a wireless power transmission method includes: forming, by a transmission coil, mutual coupling with an auxiliary coil disposed outside of a living body; and controlling a supply of power by a power source to the transmission coil to wirelessly transmit the power from the transmission coil via the auxiliary coil to a wireless power reception apparatus disposed inside the living body through the mutual coupling, wherein a distance between the transmission coil and the auxiliary coil is adjustable.

Other features and aspects will be apparent from the following detailed description, the drawings, and the claims.

Figure 1:
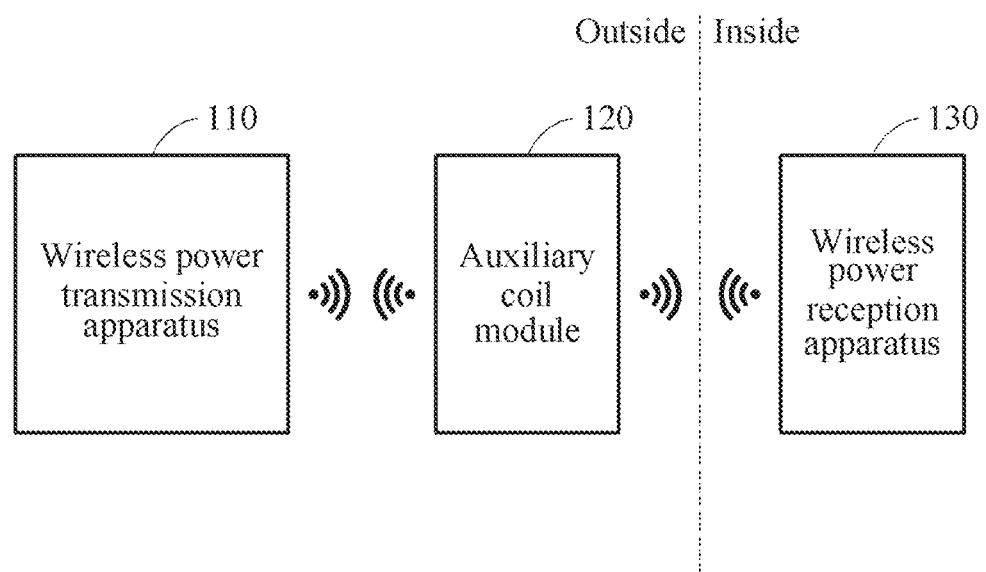
FIG. 1 illustrates an example of a wireless power transmission system.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

Throughout the specification, when an element, such as a layer, region, or substrate, is described as being "on," "connected to," or "coupled to" another element, it may be directly "on," "connected to," or "coupled to" the other element, or there may be one or more other elements intervening therebetween. In contrast, when an element is described as being "directly on," "directly connected to," or "directly coupled to" another element, there can be no other elements intervening therebetween.

The terminology used herein is for the purpose of describing particular examples only and is not to be limiting of the examples. As used herein, the singular forms "a", "an", and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

Unless otherwise defined, all terms including technical and scientific terms used herein have the same meaning as commonly understood by one of ordinary skill in the art to which this disclosure pertains and after an understanding of the disclosure of this application. It will be further understood that terms, such as those defined in commonly-used dictionaries, should be interpreted as having a meaning that is consistent with their meaning in the context of the relevant art and the disclosure of this application, and will not be interpreted in an idealized or overly formal sense unless expressly so defined herein.

When describing the examples with reference to the accompanying drawings, like reference numerals refer to like constituent elements and a repeated description related thereto will be omitted. In the description of examples, detailed description of related structures or functions will be omitted when it is deemed that such description will cause ambiguous interpretation of the present disclosure.

FIG. 1 illustrates an example of a wireless power transmission system.

Referring to FIG. 1, a wireless power transmission system 100 may wirelessly transmit power from a wireless power transmission apparatus 110 disposed outside of a living body to a wireless power reception apparatus 130 disposed inside the living body. The wireless power transmission system 100 may include the wireless power transmission apparatus 110, an auxiliary coil module 120, and the wireless power reception apparatus 130.

The wireless power transmission apparatus 110 may be disposed outside of a living body to wirelessly transmit power. For example, the wireless power transmission apparatus 110 may be a portable smart terminal such as a smart phone, a tablet, or a smart watch.

The auxiliary coil module 120 may be disposed outside of the living body to relay the power received from the wireless power transmission apparatus 110 to the wireless power reception apparatus 130 inside the living body. For example, the auxiliary coil module 120 may be coupled to the wireless power transmission apparatus 110 while being spaced by a predetermined distance apart therefrom, and/or attached to an outer surface of the living body. To attach the auxiliary coil module 120 to the outer surface of the living body, the auxiliary coil module 120 may be implemented in a form of a patch, as a non-limiting example.

The wireless power reception apparatus 130 is an apparatus disposed inside the living body to wirelessly receive power. For example, the wireless power reception apparatus 130 may be an apparatus implanted into the living body, and may perform an operation of sensing biometric information (for example, biopotentials) and/or an operation of applying electrical signals to the living body. However, the wireless power reception apparatus 130 is not limited to the example.

When the wireless power reception apparatus 130 is implanted deep into the living body and/or the wireless power reception apparatus 130 is extremely tiny, the wireless power transmission apparatus 110 may have difficulties in matching a transmission coil impedance without using an additional module. Thus, the auxiliary coil module 120 may be used to match the transmission coil impedance of the wireless power transmission apparatus 110 to a target impedance. For example, a distance between the wireless power transmission apparatus 110 and the auxiliary coil module 120 may be caused or controlled to be change, or a size of an auxiliary coil included in the auxiliary coil module 120 may be caused or controlled to be change. An example of matching the transmission coil impedance will be described in detail below.

Figure 2:
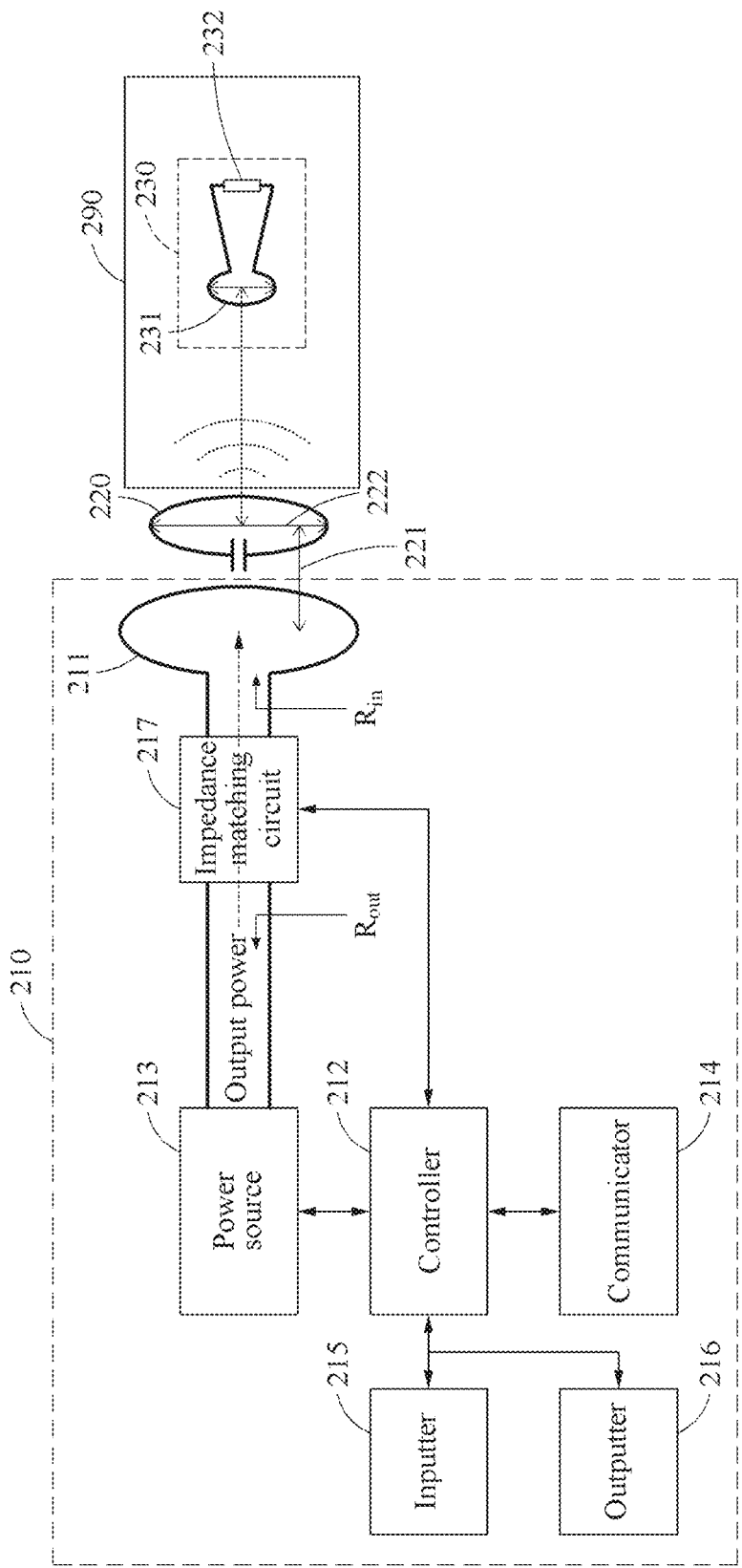
FIG. 2 illustrates an example of a configuration of a wireless power transmission apparatus.

FIG. 2 illustrates an example of a configuration of a wireless power transmission apparatus.

Referring to FIG. 2, a wireless power transmission apparatus 210 may include a transmission coil 211, a controller 212, a power source 213, a communicator 214, an inputter (e.g., an input/output (I/O) component or device) 215, an outputter (e.g., an input/output (I/O) component or device) 216, and an impedance matching circuit 217, for example.

The transmission coil 211 is a coil configured to form mutual coupling with an auxiliary coil 220 disposed outside of a living body 290. For example, a capacitor may be connected to the transmission coil 211, and resonance frequencies of the transmission coil 211 and the capacitor may be the same as or similar to a resonance frequency of the auxiliary coil 220. In response to power being supplied, the transmission coil 211 may form mutual coupling with the auxiliary coil 220, and wirelessly transmit the power to the auxiliary coil 220 through the mutual coupling.

The controller 212 controls a supply of power by the power source 213 to the transmission coil 211. For example, the controller 212 may control the supply of power, thereby wirelessly transmitting the power from the transmission coil 211 via the auxiliary coil 220 to a wireless power reception apparatus 230 disposed inside the living body 290 through the mutual coupling. The controller 212 may initiate or suspend the supply of power from the power source 213 to the transmission coil 211. Although FIG. 2 illustrates an example in which the controller 212 controls the power source 213, the present disclosure is not limited to the example. The controller 212 may also control an electrical connection between the power source 213 and the transmission coil 211.

The power source 213 supplies the power to the transmission coil 211 based on the control of the controller 212. For example, the power source 213 may generate power having an alternating current (AC) voltage.

The communicator 214 may communicate with an auxiliary coil module. For example, the communicator 214 may receive, from the auxiliary coil module, power information sensed by the auxiliary coil module, or transmit an instruction related to power transmission to the auxiliary coil module. The communicator 214 may build low-power communication (for example, near field communication (NFC) or Bluetooth low energy (BLE) communication) with the auxiliary coil module to transmit and receive the information.

The inputter 215 receives an input from a user. For example, the inputter 215 may include a keyboard configured to receive a keystroke input by the user, or a touch screen or a touch pad configured to receive a touch manipulation input by the user. Further, the inputter 215 may include a microphone configured to receive a voice of the user being input. For example, the inputter 215 may receive, from the user, a power transmission input indicating that the power is to be transmitted from the wireless power transmission apparatus 210 to the wireless power reception apparatus 230. In response to the power transmission input being received from the user through the inputter 215, the controller 212 may transmit the power from the power source 213 to the transmission coil 211.

The outputter 216 outputs information related to wireless power transmission for the user. For example, the outputter 216 may output, for the user, an indication that the wireless power transmission apparatus 210 is to be repositioned, or an indication that the position of the wireless power transmission apparatus 210 is to be maintained. The outputter 216 may output any one or any combination of visual information, haptic information, and acoustic information.

The impedance matching circuit 217 matches an output impedance $R_{out}$ of the wireless power transmission apparatus 210 to the target impedance. Herein, the output impedance $R_{out}$ of the wireless power transmission apparatus 210 is an impedance measured when the power source 213 is observed from the impedance matching circuit 217. In an example, the target impedance may be configured to be 50 ohm. However, the target impedance is not limited to the example, and examples exist herein with varying target impedances. An impedance measured when the transmission coil 211 is viewed based on the impedance matching circuit 217 is referred to as a transmission coil impedance $R_{in}$. When the transmission coil impedance $R_{in}$ is matched to have a value the same as or similar to the target impedance, a loss occurring when the power output from the power source 213 is transmitted to the transmission coil 211 may be minimized. That is, the power output from the power source 213 may be reflected at an input terminal of the transmission coil 211 when the transmission coil impedance $R_{in}$ is mismatched to the target impedance, and thus, such power reflection may be minimized when the transmission coil impedance $R_{in}$ is matched to the target impedance. The transmission coil impedance $R_{in}$ of the wireless power transmission apparatus 210 will be described further below with reference to FIG. 12.

The transmission coil 211 may have a structure with a weakly-coupled coupling coefficient less than a threshold value with respect to a reception coil 231. For example, a size of the transmission coil 211 may be greater than a size of the reception coil 231 of the wireless power reception apparatus 230. In an example, the threshold value may be "0.1". However, the threshold value is not limited to the example.

Figure 12:
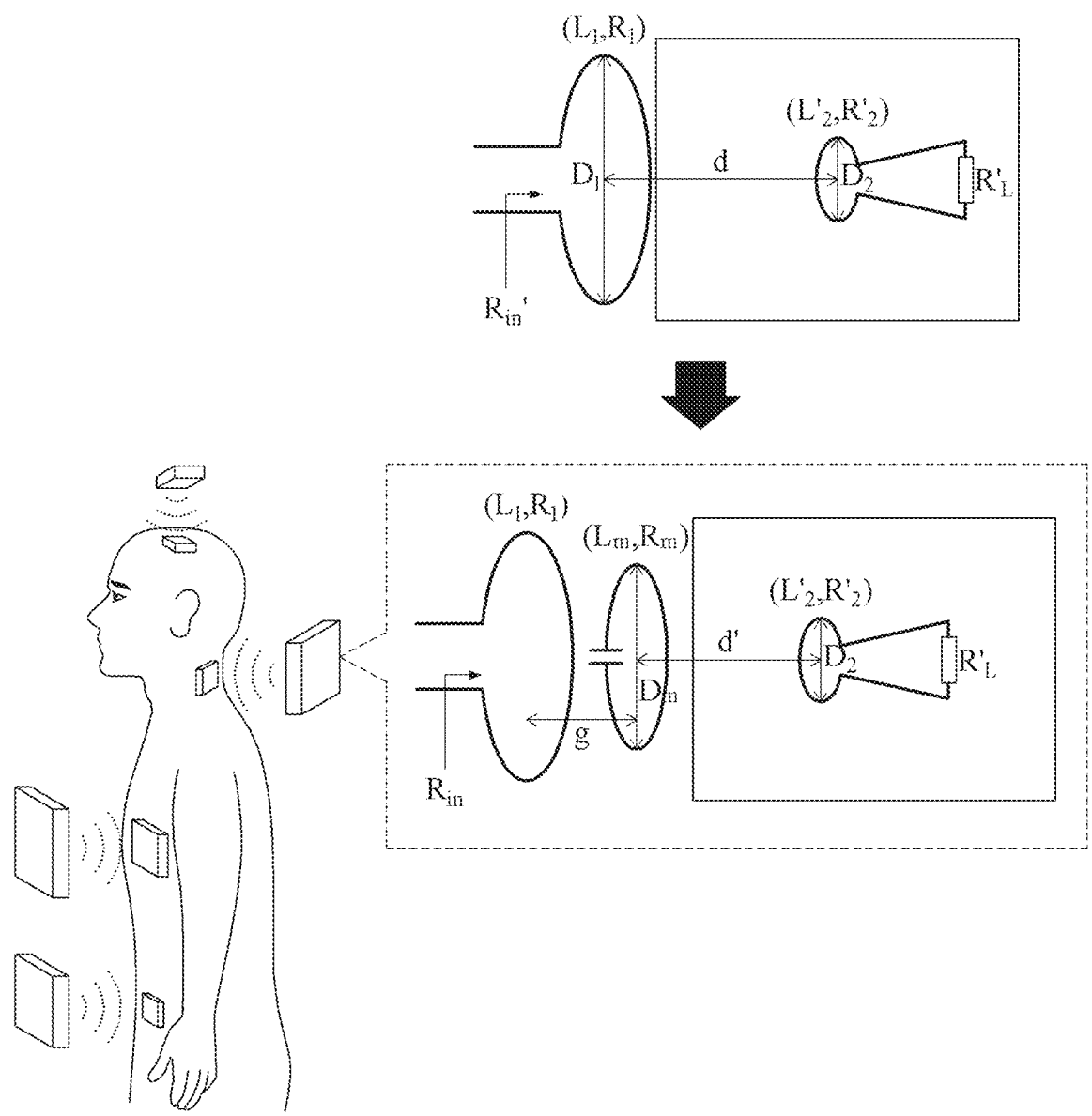
FIG. 12 illustrates an example of matching a transmission coil impedance of a wireless power transmission apparatus and an output impedance.

For reference, in a typical wireless power transmission apparatus that does not include an auxiliary coil module of one or more embodiments of the present disclosure, it may be difficult to match a transmission coil impedance $R_{in}$ to the target impedance using only a transmission coil (e.g., the transmission coil 211) and a reception coil (e.g., the reception coil 231) due to weak mutual coupling between the transmission coil and the reception coil, an example of which will be described further below with reference to FIG. 12. When a distance between the transmission coil 211 and the reception coil 231 of the typical wireless power transmission apparatus increases in response to an activity of a living body, or when the size of the reception coil 231 is relatively small, it may be difficult to match the transmission coil impedance $R_{in}$ to the target impedance.

On the contrary, the transmission coil impedance of the wireless power transmission apparatus 210 of one or more embodiments of the present disclosure is effectively matched to the target impedance through the auxiliary coil module. Based on the position of the transmission coil 211 disposed outside of the living body 290, the position of the auxiliary coil 220 outside of the living body 290, the size of the reception coil 231 inside the living body 290, and the depth of the reception coil 231 inside the living body 290, the auxiliary coil 220 of an appropriate size may be positioned at an appropriate distance 221 from the transmission coil 211. Through a selection and/or configuration of a size 222 of the auxiliary coil 220 in the wireless power transmission apparatus 210 and an adjustment and/or managed configuration of the distance 221 between the transmission coil 211 and the auxiliary coil 220, the transmission coil impedance $R_{in}$ may be effectively matched to the target impedance. Thus, a reduction of the output power transmitted from the power source 213 to the transmission coil 211 is advantageously prevented.

The auxiliary coil module includes at least one auxiliary coil 220. In an example, the auxiliary coil module may be attached to the surface of the living body 290. The auxiliary coil module may be implemented in a form of a patch including a flexible material and attached to human skin. In another example, the auxiliary coil module may include a housing configured to maintain the distance 221 between the transmission coil 211 and the auxiliary coil 220. In this example, the auxiliary coil module may be configured to be replaceable with another auxiliary coil module including an auxiliary coil 220 of a different size (e.g., of a different diameter or covering a different sized area) and being at a different distance from the wireless power transmission apparatus 210, or configured such that the housing of the auxiliary coil module adjusts the distance 221. The distance 221 between the transmission coil 211 and the auxiliary coil 220 may be adjustable.

The wireless power reception apparatus 230 includes the reception coil 231 and a load 232. The wireless power reception apparatus 230 transmits the received power to the load 232 through the reception coil 231.

For reference, a respective capacitor (e.g., a collective capacitance of one or more capacitors) may be connected separately to the transmission coil 211, the auxiliary coil 220, and the reception coil 231. A structure in which the capacitor is connected with the transmission coil 211 is referred to as a transmission resonator, a structure in which the capacitor is connected with the auxiliary coil 220 is referred to as an auxiliary resonator, and a structure in which the capacitor is connected with the reception coil 231 is referred to as a reception resonator. Resonance frequencies of the transmission resonator, the auxiliary resonator, and the reception resonator may be the same or similar to each other for effective coupling. Thus, a combination of the transmission resonator and the auxiliary resonator may form mutual coupling, and a combination of the auxiliary resonator and the reception resonator may form mutual coupling. Mutual coupling is also referred to as mutual resonance. However, the transmission resonator and the reception resonator may have a weakly-coupled coupling coefficient less than a threshold value, and weak (or low) mutual coupling may be formed between the transmission resonator and the reception resonator. When compared to the mutual coupling between the transmission resonator and the auxiliary resonator and the mutual coupling between the auxiliary resonator and the reception resonator, the mutual coupling between the transmission resonator and the reception resonator may be considerably weak and thus, negligible, which will be described further below with reference to FIG. 12.

FIG. 2 illustrates an example in which the auxiliary coil 220 is provided in a form of a circular loop, and the size 222 of the auxiliary coil 220 corresponds to the diameter of the circular loop. However, the present disclosure is not limited to the example, and, in one or more other examples, the auxiliary coil 220 may be of a shape other than a circular loop (e.g., an elliptical or rectangular-shaped coil), wherein the size 220 corresponds to a length or width of the auxiliary coil 220.

Hereinafter, examples of changing the distance 221 between the wireless power transmission apparatus 210 and the auxiliary coil 220 and changing the size 222 of the auxiliary coil 220 will be described.

Figure 3:
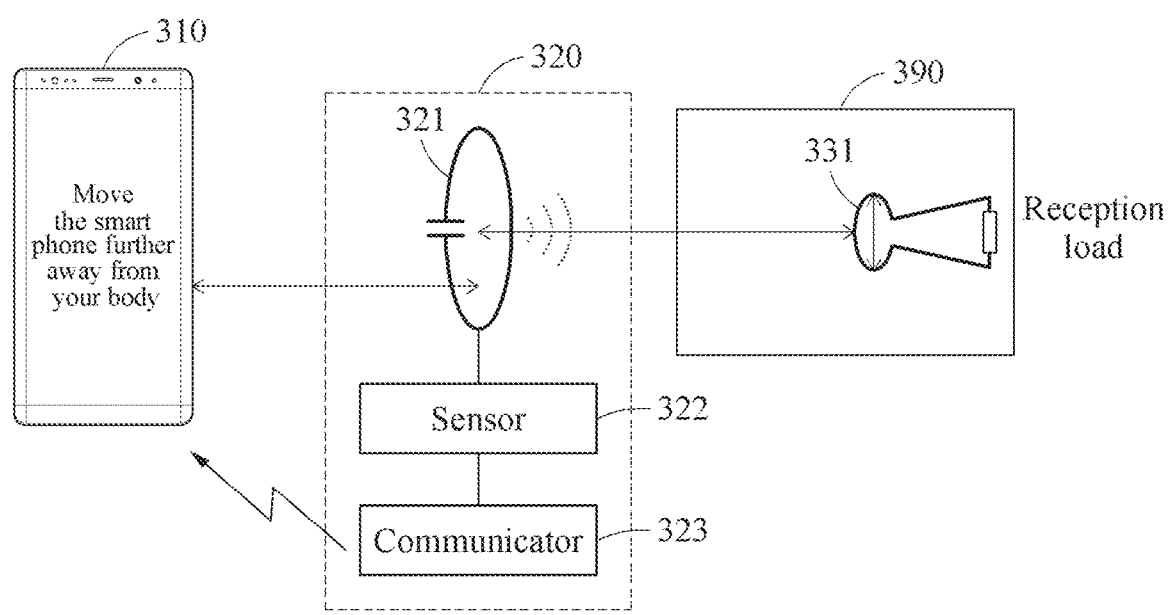
FIG. 3 illustrates an example of changing a distance between a wireless power transmission apparatus and an auxiliary coil module.

FIG. 3 illustrates an example of changing a distance between a wireless power transmission apparatus and an auxiliary coil module.

Referring to FIG. 3, an auxiliary coil module 320 may further include a sensor 322 and a communicator 323, in addition to an auxiliary coil 321.

The sensor 322 of the auxiliary coil module 320 senses power information from the auxiliary coil 321. For example, the sensor 322 may sense, as the power information, a magnitude of a voltage applied to the auxiliary coil 321, a magnitude of a current flowing in the auxiliary coil 321, and/or a magnitude of a magnetic field emitted from the auxiliary coil 321.

The communicator 323 of the auxiliary coil module 320 transmits the sensed power information to a wireless power transmission apparatus 310. For example, as described with reference to FIG. 2, the communicator 323 of the auxiliary coil module 320 may generate NFC or BLE communication with the wireless power transmission apparatus 310 to transmit and receive the information. Thus, in examples, such communicators herein may be NFC and/or BLE communicator modules.

A communicator of the wireless power transmission apparatus 310 receives power information related to power of the auxiliary coil 321 from the auxiliary coil module 320 including the auxiliary coil 321.

A controller of the wireless power transmission apparatus 310 may output guidance information indicating an instruction to either change or maintain a distance between a transmission coil of the wireless power transmission apparatus 310 and the auxiliary coil 321 of the auxiliary coil module 320 based on the power information. In the example of FIG. 3, guidance information indicating that the wireless power transmission apparatus 310 is to be moved to a distance farther from a living body 390 is output in a form of visual information.

The controller may determine whether a transmission coil impedance of the wireless power transmission apparatus 310 is matched to a target impedance based on the power information received from the auxiliary coil module 320. For example, the controller may determine that the transmission coil impedance is matched to the target impedance when the power information sensed from the auxiliary coil 321 represents a maximum power magnitude (for example, a maximum voltage magnitude, a maximum current magnitude, and/or a maximum magnetic field magnitude) while the distance between the wireless power transmission apparatus 310 and the auxiliary coil 321 and the size of the auxiliary coil 321 are being changed. That is because, when the transmission coil impedance is matched to the target impedance, a loss at the transmission coil may be minimized, and thus the power transmitted to the auxiliary coil 321 may be maximized.

For example, the communicator of the wireless power transmission apparatus 310 may collect power information from the auxiliary coil module 320 at a plurality of, or incremental, distances of the wireless power transmission apparatus 310 with respect to the auxiliary coil 321, while the wireless power transmission apparatus 310 moves in one direction with respect to the auxiliary coil 321. The controller of the wireless power transmission apparatus 310 may then determine a distance at which a maximum magnitude is sensed, among the plurality of distances of the wireless power transmission apparatus 310 with respect to the auxiliary coil 321, based on the collected power information. An outputter of the wireless power transmission apparatus 310 may output an indication that the distance at which the maximum magnitude is sensed is to be maintained. Thus, the wireless power transmission apparatus 310 may transmit power to a reception coil 331 via the auxiliary coil 321, at a distance at which the transmission coil impedance is matched to the target impedance.

However, the present disclosure is not limited to the above example. For example, when the wireless power transmission apparatus 310 is configured to autonomously measure the transmission coil impedance, the wireless power transmission apparatus 310 may determine whether the measured transmission coil impedance is matched to the target impedance, without using the power information of the auxiliary coil 321.

Figure 4:
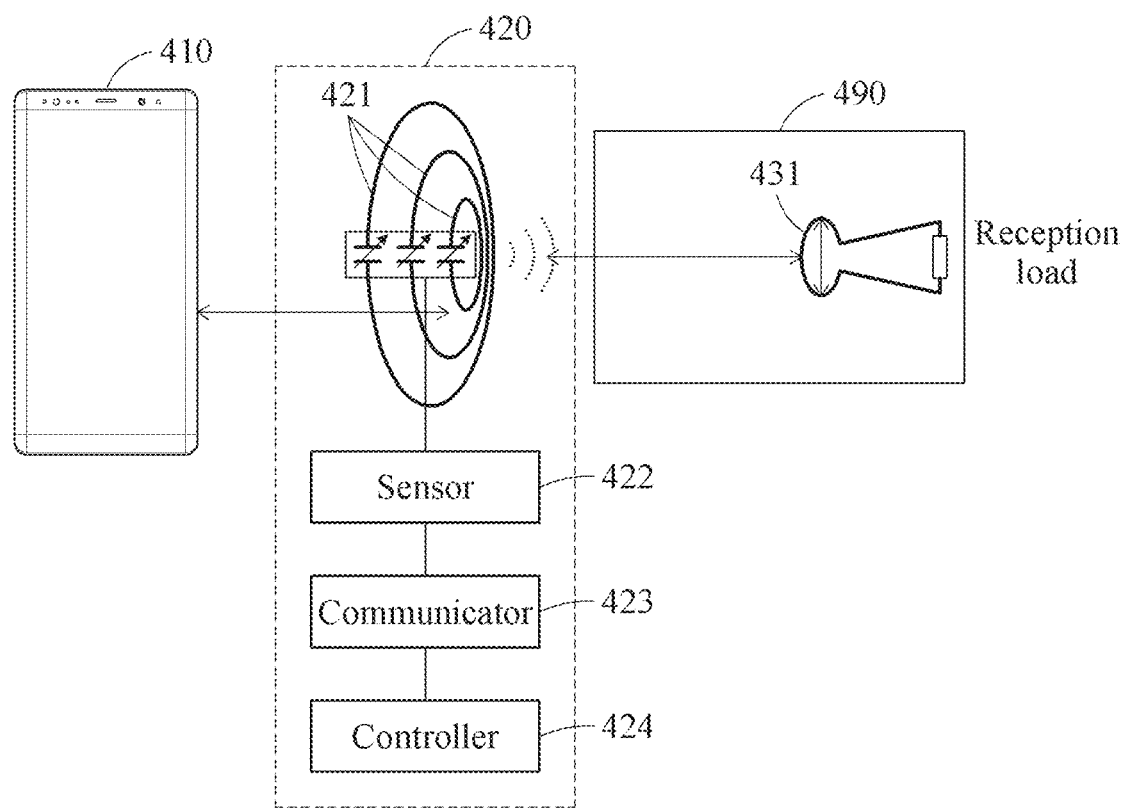
FIG. 4 illustrates an example of an auxiliary coil module including a plurality of auxiliary coils.

FIG. 4 illustrates an example of an auxiliary coil module including a plurality of auxiliary coils.

Referring to FIG. 4, an auxiliary coil module 420 includes a plurality of auxiliary coils 421. Each of the plurality of auxiliary coils 421 is provided in a different size. A variable capacitor is connected to each of the auxiliary coils 421. A capacitance of the variable capacitor changes based on a voltage. A controller 424 of the auxiliary coil module 420 may selectively activate or deactivate each auxiliary coil by controlling an adjusting of the capacitance of the variable capacitor connected to each of the auxiliary coils 421. For example, the controller 424 of the auxiliary coil module 420 may adjust a variable capacitor connected to one of the plurality of auxiliary coils 421, thereby matching a resonance frequency of the one auxiliary coil to a resonance frequency of a transmission coil. The controller 424 of the auxiliary coil module 420 may control variable capacitors connected to the remaining auxiliary coils, thereby changing resonance frequencies of the remaining auxiliary coils to be different from the resonance frequency of the transmission coil. In an example, power may be transmitted only when the resonance frequencies are matched, and thus only the auxiliary coil of which the resonance frequency is matched is activated, and the remaining auxiliary coils are deactivated. For example, the controller 424 of the auxiliary coil module 420 may activate or deactivate the auxiliary coil based on a signal received from a wireless power transmission apparatus 410. However, the present disclosure is not limited to the example. For example, the controller 424 of the auxiliary coil module 420 may also autonomously select an auxiliary coil to be activated. Further, switches may be used instead of the variable capacitors.

A sensor 422 and a communicator 423 may operate similarly to the sensor 322 and the communicator 323 of FIG. 3.

A communicator of the wireless power transmission apparatus 410 may transmit, to the auxiliary coil module 420 including the auxiliary coils 421 of a plurality of sizes, a signal to activate one of the auxiliary coils 421. A controller of the wireless power transmission apparatus 410 may select one auxiliary coil from the auxiliary coils 421 of the plurality of sizes in the auxiliary coil module 420 based on power information received from the auxiliary coil module 420. The communicator of the wireless power transmission apparatus 410 may transmit a signal to activate the selected auxiliary coil. For example, the communicator of the wireless power transmission apparatus 410 may transmit signals to sequentially activate the auxiliary coils 421 to the auxiliary coil module 420, and may sequentially receive respective power information related to the auxiliary coils 421 sensed by the auxiliary coil module 420. The controller of the wireless power transmission apparatus 410 may then select an auxiliary coil at which a maximum magnitude is sensed, from the auxiliary coils 421. Thus, even when a distance between the wireless power transmission apparatus 410 and the auxiliary coil module 420 changes, the wireless power transmission apparatus 410 may dynamically select the size of the auxiliary coil, and may transmit power to a reception coil 431 inside a living body 490 in a state of optimal transmission coil impedance.

Figure 5:
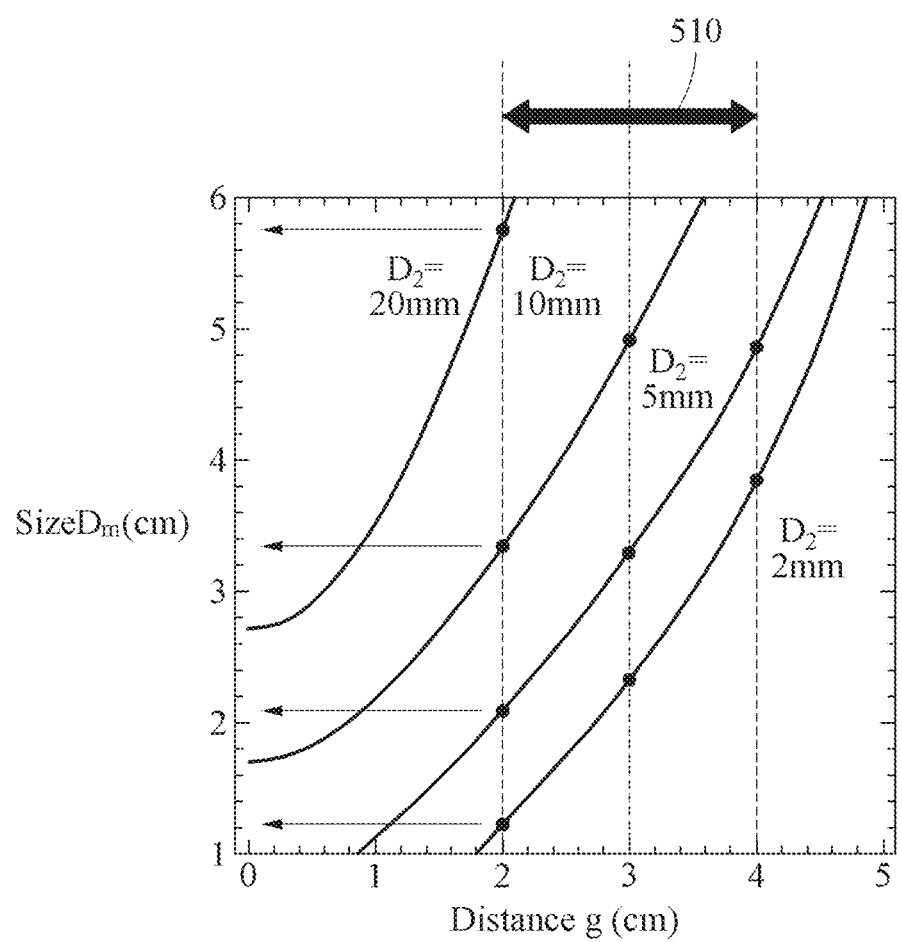
FIG. 5 illustrates an example of a size of a reception coil, a size of an auxiliary coil, and a distance between a transmission coil and the auxiliary coil satisfying a target impedance.

FIG. 5 illustrates an example of a size of a reception coil, a size of an auxiliary coil, and a distance between a transmission coil and the auxiliary coil satisfying a target impedance.

A graph of FIG. 5 illustrates a relationship of a distance g between an auxiliary coil and a wireless power transmission apparatus, a size $D_m$, of the auxiliary coil, and a size $D_2$ of a reception coil, under the condition that a transmission coil impedance satisfies a target impedance of 50 ohm. A distance between the auxiliary coil and the reception coil may be d=1 cm. According to the graph of FIG. 5 illustrating the relationship between the distance g and the size $D_m$ of the auxiliary coil based on Equation 3 (which will be described with reference to FIG. 12), the size $D_m$ of the auxiliary coil may be greater than or equal to about 1.2 centimeters (cm) to achieve the example target impedance of 50 ohm. When the size $D_m$ of the auxiliary coil is less than 1.2 cm, there may not be a solution satisfying the transmission coil impedance $R_{in}$ of 50 ohm in Equation 3. To satisfy the graph of FIG. 5, by setting the appropriate size $D_m$ of the auxiliary coil and the distance g corresponding thereto (for example, the size of 2.6 cm, and the distance of 2 cm), the transmission coil impedance $R_{in}$ may be matched to the target impedance of 50 ohm to which the output impedance is matched.

For practical use, an auxiliary coil module may be attached to a surface of a living body and the wireless power transmission apparatus may be spaced by a predetermined distance (for example, 2 cm) away from the surface. As non-limiting examples, according to the graph of FIG. 5, when the size of the reception coil is $D_2=2$ mm at a distance g=2 cm, an auxiliary coil having a size of $D_m=1.2$ cm may be used; when the size of the reception coil is $D_2=5$ mm at a distance g=2 cm, an auxiliary coil having a size of $D_m=2$ cm may be used; when the size of the reception coil is $D_2=10$ mm at a distance g=2 cm, an auxiliary coil having a size of $D_m=3.4$ cm is used; and when the size of the reception coil is $D_2=20$ mm at a distance g=2 cm, an auxiliary coil having a size of $D_m=6$ cm may be used. Thus, the user may select an auxiliary coil of a size most or more appropriate for the size of the reception coil currently implanted into a living body and attach the selected auxiliary coil to the wireless power transmission apparatus or the surface of the living body for use.

In another example, the auxiliary coil module may implemented in a structure including a plurality of auxiliary coils of a plurality of sizes, as shown in FIG. 4. In this example, a controller of the wireless power transmission apparatus may select an auxiliary coil corresponding to a predetermined distance (for example, g=2 cm in FIG. 5) and a predetermined size of a reception coil included in a wireless power reception apparatus, from the auxiliary coils of the plurality of sizes. For example, the coils may have a relationship according to the graph of FIG. 5 wherein the distance is g=2 cm. In this non-limiting example, the controller may select an auxiliary coil having a size of $D_m=1.2$ cm when the size of the reception coil is $D_2=2$ mm, an auxiliary coil having a size of $D_m=2$ cm when the size of the reception coil is $D_2=5$ mm, an auxiliary coil having a size of $D_m=3.4$ cm when the size of the reception coil is $D_{2=10}$ mm, and an auxiliary coil having a size of $D_m=6$ cm when the size of the reception coil is $D_2=20$ mm. A communicator of the wireless power transmission apparatus may transmit a signal to activate the selected auxiliary coil to the auxiliary coil module. Thus, the wireless power transmission apparatus may immediately activate an auxiliary coil which implements an optimal transmission coil impedance, thereby implementing fast power transmission to a wireless power reception apparatus inside the living body without a loss.

Furthermore, the controller may select an auxiliary coil which matches the transmission coil impedance to the target impedance, from the plurality of auxiliary coils, in response to a distance change 510. In an example of FIG. 5, the distance may change to g=3 cm and to g=4 cm. As shown in FIG. 5, the controller selects an auxiliary coil of the size $D_m$ corresponding to a point at which a curve corresponding to the size $D_2=2$ mm, 5 mm, 10 mm, 20 mm of each reception coil and a straight line of g=3 cm, 4 cm are determined to intersect.

Figure 6:
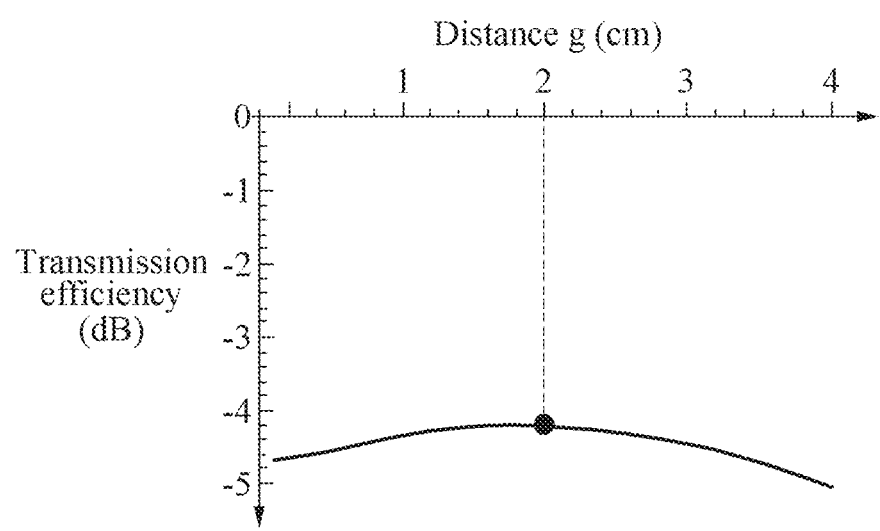
FIG. 6 illustrates an example of a relationship between a distance and a power transmission efficiency under a condition that a target impedance is satisfied.

FIG. 6 illustrates an example of a relationship between a distance and a power transmission efficiency under the condition that a target impedance is satisfied.

In FIG. 6, a horizontal axis indicates a distance g between a wireless power transmission apparatus and an auxiliary coil, and a vertical axis indicates a transmission efficiency. As described with reference to FIG. 5, when calculating a transmission coil impedance to satisfy a target impedance of 50 ohm, the transmission efficiency curve changes based on the distance g as shown in FIG. 6. In the example of FIG. 6, the optimal transmission efficiency appears at the distance g=2 cm.

Figure 7:
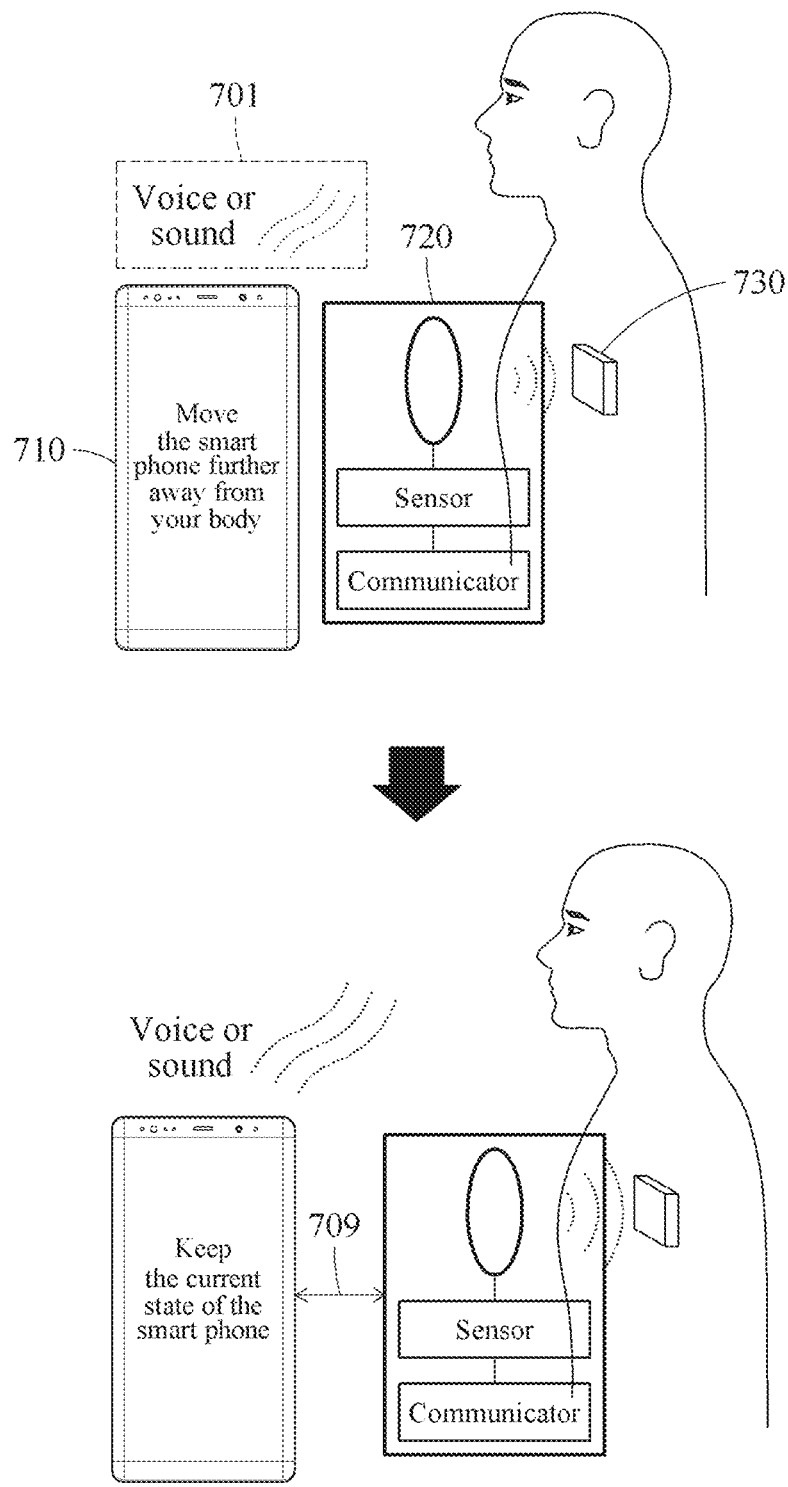
FIG. 7 illustrates an example of an auxiliary coil module attached to a living body.

FIG. 7 illustrates an example of an auxiliary coil module attached to a living body.

As described with reference to FIG. 3, a wireless power transmission apparatus 710 may output guidance information indicating an instruction to either change or maintain a distance between a transmission coil and an auxiliary coil based on power information through an outputter. For example, as shown in FIG. 7, an auxiliary coil module 720 may be attached to a surface of the living body, and the wireless power transmission apparatus 710 may be moved by a user to be closer to or further away from the auxiliary coil module 720. Thus, a distance between the wireless power transmission apparatus 710 and the auxiliary coil module 720 may be adjusted.

The outputter may output, for the user, an indication that the wireless power transmission apparatus 710 is to be moved in one direction and/or an indication that the wireless power transmission apparatus 710 is to be held at a distance 709 at which a maximum magnitude is sensed, to collect the power information. For example, the outputter may output, as visual information or acoustic information 701, an indication that the wireless power transmission apparatus 710 is to be moved in a direction away from the surface of the living body while collecting the power information. In another example, the outputter may output, as the visual information or acoustic information 701, an indication that the wireless power transmission apparatus 710 is to be held to maintain a current position of the wireless power transmission apparatus 710 when the current position corresponds to the distance 709 at which the maximum magnitude is sensed. Thus, when the user moves the wireless power transmission apparatus 710, the wireless power transmission apparatus 710 may transmit power to a wireless power reception apparatus 730 at an optimal transmission coil impedance.

Further, the wireless power transmission apparatus 710 may activate an auxiliary coil having a size and being at a distance representing a maximum magnitude, in response to the power information, for example, a voltage, a current, and/or a magnetic field magnitude, corresponding to a maximum magnitude. Thus, the wireless power transmission apparatus 710 may transmit power to the wireless power reception apparatus 730 via the auxiliary coil after the transmission coil impedance is matched.

Figure 8:
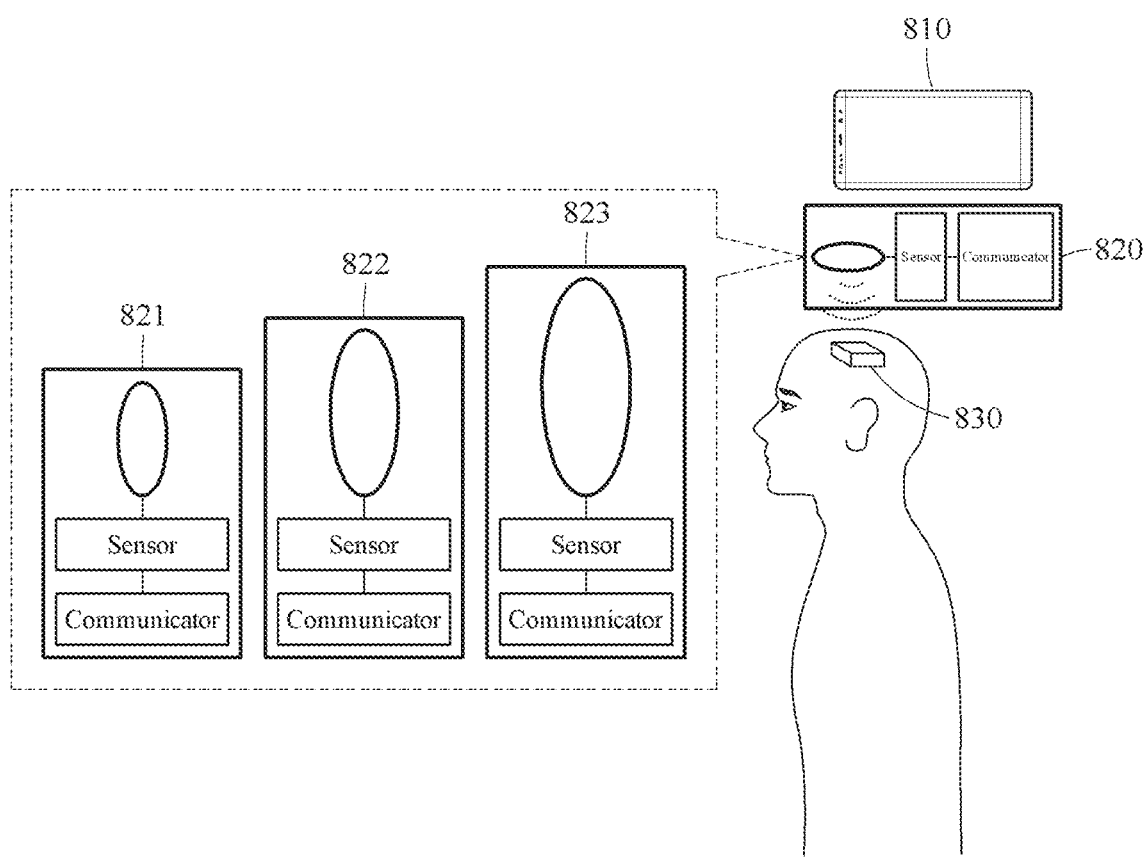
FIG. 8 illustrates an example of replacing an auxiliary coil module to be attached to a living body.

FIG. 8 illustrates an example of replacing an auxiliary coil module to be attached to a living body.

An auxiliary coil is replaceable with a coil of a different size. For example, a user may select a size of an auxiliary coil, among a plurality of auxiliary coils 821, 822, and 823, in view of a depth of a wireless power reception apparatus 830 implanted into an individual body, a position of a wireless power transmission apparatus 810, and/or a change in distance from an auxiliary coil module 820. The user may attach the auxiliary coil module 820 including an auxiliary coil having the selected size to the surface of the living body.

The wireless power transmission apparatus 810 may output power information sensed by the auxiliary coil module 820 through an outputter. For example, the wireless power transmission apparatus 810 may output magnitudes of a voltage, a current, and/or a magnetic field of the auxiliary coil through the outputter. Thus, the user may directly verify a transmission state.

Figure 9:
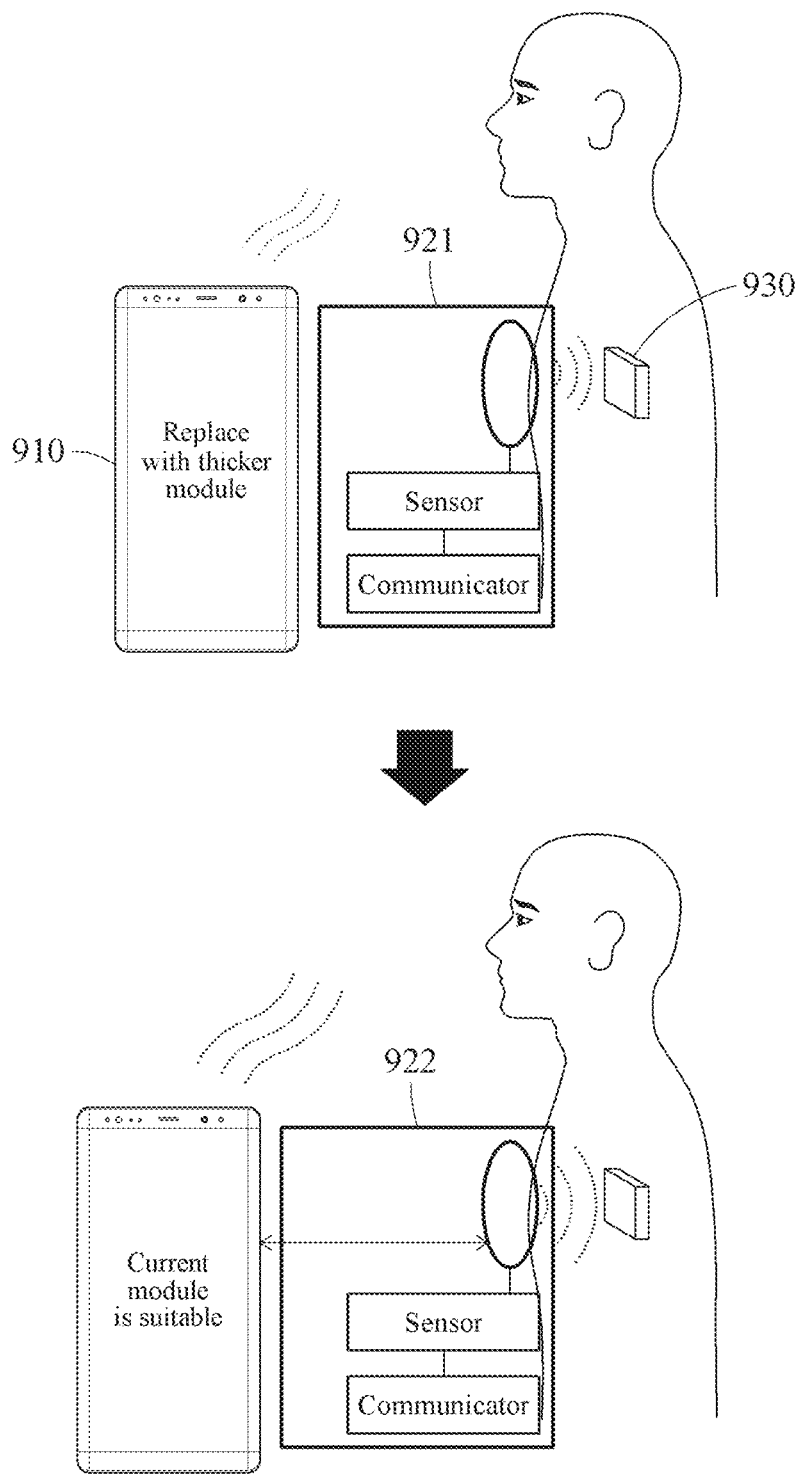
FIG. 9 illustrates an example of coupling an auxiliary coil module to a wireless power transmission apparatus.

FIG. 9 illustrates an example of coupling an auxiliary coil module to a wireless power transmission apparatus.

An auxiliary coil module may be implemented in a structure to be coupled to a wireless power transmission apparatus 910 (for example, a smart phone). The auxiliary coil module may be configured to be attachable to and detachable from the wireless power transmission apparatus 910. Thus, the auxiliary coil module may be configured to be replaceable in the wireless power transmission apparatus 910. The above descriptions with respect to the wireless power transmission apparatuses and auxiliary coils of FIGS. 1-8 are also applicable to the discussion of FIGS. 9-12.

The wireless power transmission apparatus 910 may detect whether the auxiliary coil module is attached to at least one surface of the wireless power transmission apparatus 910. When a predetermined auxiliary coil module (e.g., which was previously determined by the wireless power transmission apparatus 910 to be attached to the wireless power transmission apparatus 910) is attached and then detached and another auxiliary coil module is attached, the wireless power transmission apparatus 910 may determine that the auxiliary coil module has been replaced.

In response to the auxiliary coil module being replaced with a new auxiliary coil module, a controller of the wireless power transmission apparatus 910 may determine whether to replace the new auxiliary coil module based on whether a transmission coil impedance changed by the new auxiliary coil module reaches a target impedance. For example, in response to the transmission coil impedance reaching the target impedance, the controller may determine to maintain the new auxiliary coil module. As another example, in response to the transmission coil impedance not reaching the target impedance, the controller may determine to replace the new auxiliary coil module currently attached. An outputter of the wireless power transmission apparatus 910 may output one of a replacement indication and a maintenance indication of the auxiliary coil module.

In addition, the controller of the wireless power transmission apparatus 910 may determine whether the transmission coil impedance reaches the target impedance, based on power information (for example, a voltage magnitude, a current magnitude, and/or a magnetic field magnitude) sensed by the auxiliary coil module. For example, the controller of the wireless power transmission apparatus 910 may determine that the transmission coil impedance reaches the target impedance in response to the power information sensed by the auxiliary coil module reaching target power information designated for the auxiliary coil module (for example, the power information reaching a predetermined threshold). In a case of the voltage magnitude being the power information, the wireless power transmission apparatus 910 may determine that the transmission coil impedance reaches the target impedance in response to the voltage magnitude of the auxiliary coil sensed by the auxiliary coil module reaching a target voltage. The target power information may be designated for each individual auxiliary coil module. The auxiliary coil module may include auxiliary coils of various sizes and may be at various distances, which will be described later with reference to FIG. 10.

However, the present disclosure is not limited to the example. For example, the wireless power transmission apparatus 910 may sequentially select the plurality of auxiliary coil modules, and indicate, for the user, that the selected auxiliary coil modules are to be sequentially mounted. The wireless power transmission apparatus 910 may collect the power information each time an auxiliary coil module is mounted, and determine an auxiliary coil module representing power information of a maximum magnitude based on the collected power information. The wireless power transmission apparatus 910 may indicate, for the user, that the auxiliary coil module for which the power information of the maximum magnitude is sensed is to be mounted.

In the example of FIG. 9, when a first auxiliary coil module 921 is mounted on the wireless power transmission apparatus 910, the wireless power transmission apparatus 910 may determine that the transmission coil impedance does not reach the target impedance based on power information received from the first auxiliary coil module 921. Thus, the wireless power transmission apparatus 910 may display a replacement indication through the outputter. Then, in response, the user may detach the first auxiliary coil module 921 from the wireless power transmission apparatus 910, and attach a second auxiliary coil module 922. The wireless power transmission apparatus 910 may determine that the transmission coil impedance reaches the target impedance based on power information received from the second auxiliary coil module 922. Thus, the wireless power transmission apparatus 910 may display a maintenance indication through the outputter.

The user may intuitively recognize that an auxiliary coil module of an appropriate size and at an appropriate distance is mounted through the outputter of the wireless power transmission apparatus 910. Then, in response to the impedance matching, the wireless power transmission apparatus 910 transmits power to a wireless power reception apparatus 930 while minimizing a loss.

Figure 10:
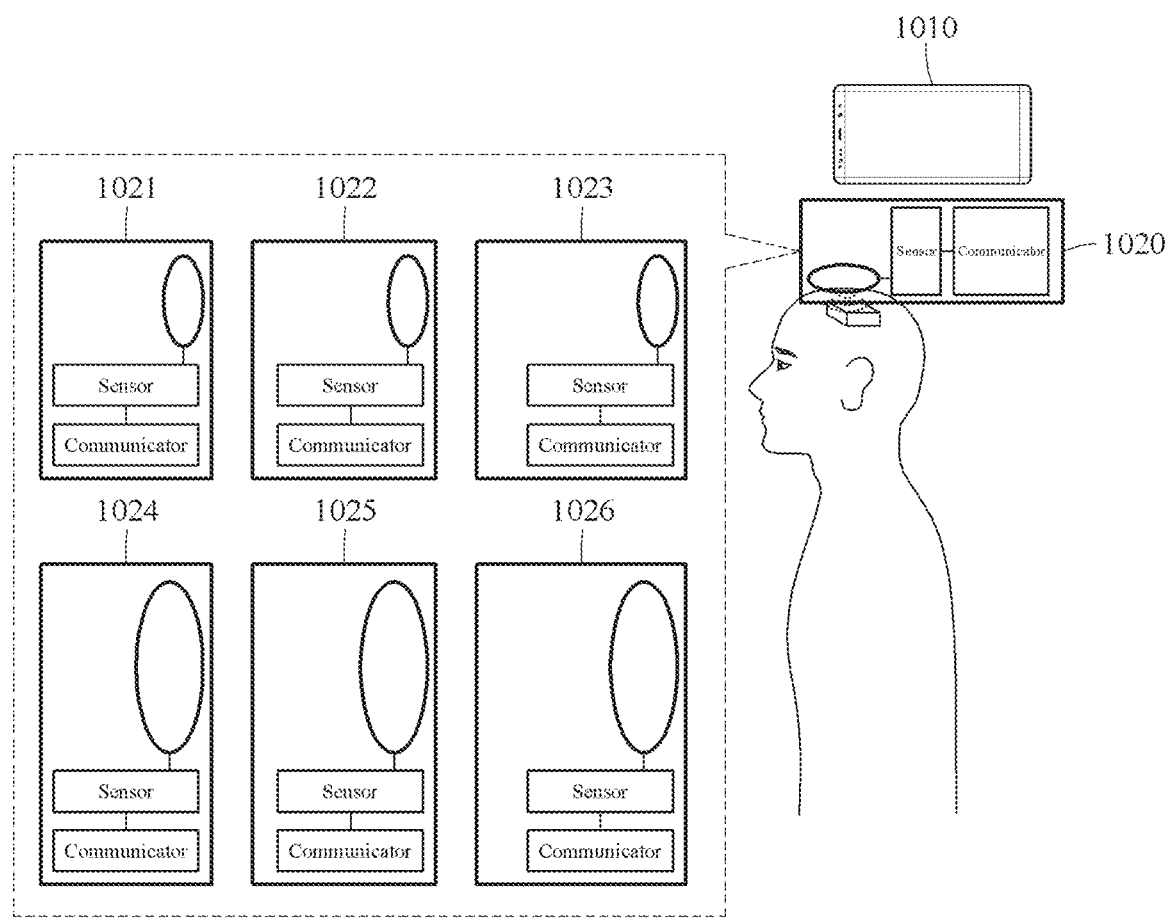
FIG. 10 illustrates an example of replacing an auxiliary coil module coupled to a wireless power transmission apparatus.

FIG. 10 illustrates an example of replacing an auxiliary coil module coupled to a wireless power transmission apparatus.

Referring to FIG. 10, an auxiliary coil module 1020 includes an auxiliary coil, and supports the auxiliary coil spaced by a predetermined distance away from a wireless power transmission apparatus 1010. The auxiliary coil module 1020 is configured to be attachable to and detachable from the wireless power transmission apparatus 1010. For example, the auxiliary coil module 1020 may be configured to be replaceable with another auxiliary coil module of a structure including an auxiliary coil of a different size and being at a different distance from the wireless power transmission apparatus 1010.

Auxiliary coil modules 1021, 1022, 1023, 1024, 1025, and 1026 of FIG. 10 may have various sizes and thus their respective auxiliary coils may be located at various distances from the wireless power transmission apparatus 1010. The first auxiliary coil module 1021, the second auxiliary coil module 1022, and the third auxiliary coil module 1023 may include auxiliary coils of the same size, but the auxiliary coils may be spaced by different distances away from the wireless power transmission apparatus 1010 due to the different sizes of the first auxiliary coil module 1021, the second auxiliary coil module 1022, and the third auxiliary coil module 1023. Likewise, the fourth auxiliary coil module 1024, the fifth auxiliary coil module 1025, and the sixth auxiliary coil module 1026 may include auxiliary coils of the same size, but the auxiliary coils may be spaced by different distances away from the wireless power transmission apparatus 1010 due to the different sizes of the fourth auxiliary coil module 1024, the fifth auxiliary coil module 1025, and the sixth auxiliary coil module 1026. The size of the auxiliary coils included in the first auxiliary coil module 1021, the second auxiliary coil module 1022, and the third auxiliary coil module 1023 may be different from the size of the auxiliary coils included in the fourth auxiliary coil module 1024, the fifth auxiliary coil module 1025, and the sixth auxiliary coil module 1026.

Thus, when a user selects an appropriate auxiliary coil module 1020 from the auxiliary coil modules of various sizes and at various distances and mounts the selected auxiliary coil module 1020 on the wireless power transmission apparatus 1010, the wireless power transmission apparatus 1010 may perform wireless power transmission in a state in which the transmission coil impedance is matched to the target impedance.

Figure 11:
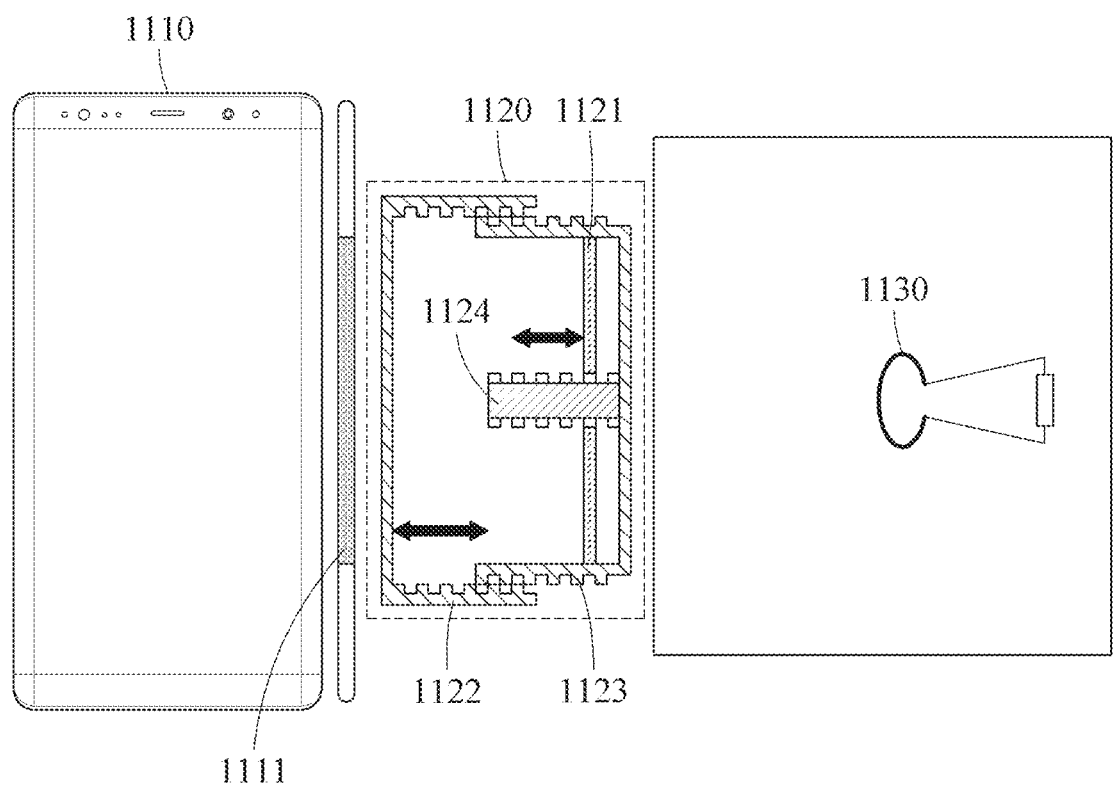
FIG. 11 illustrates an example of a structure of a connector configured to adjust a distance between a wireless power transmission apparatus and an auxiliary coil.

FIG. 11 illustrates an example of a structure of a connector configured to adjust a distance between a wireless power transmission apparatus and an auxiliary coil.

An auxiliary coil module 1120 attached to a wireless power transmission apparatus 1110 includes a connector. The connector is configured to connect the wireless power transmission apparatus 1110 and an auxiliary coil 1121, and to adjust a distance between the wireless power transmission apparatus 1110 and the auxiliary coil 1121.

The connector may include a first housing 1122 and a second housing 1123 configured to move relative to each other. The first housing 1122 includes one surface to be attached to the wireless power transmission apparatus 1110. The second housing 1123 is rotatably connected to the first housing 1122 and configured to rotate such that a distance between one surface of the second housing 1123 and one surface of the first housing 1122 changes. For example, thread grooves may be formed on an inner circumferential surface of the first housing 1122, and threads may be formed on an outer circumferential surface of the second housing 1123. The thread grooves formed on the inner circumferential surface of the first housing 1122 and the threads formed on the outer circumferential surface of the second housing 1123 may engage with each other. When at least one of the first housing 1122 and the second housing 1123 rotates, a distance between the two housings may change. The auxiliary coil 1121 is disposed parallel with one surface of the second housing 1123. Thus, the auxiliary coil 1121 is disposed parallel with a transmission coil 1111 disposed in the wireless power transmission apparatus 1110. For reference, the formation of the thread grooves and the threads on the first housing 1122 and the second housing 1123 is an example only. The thread grooves and the threads may be formed reversely, or a different engagement structure may be applied thereto.

The second housing 1123 further may include a coil supporting member 1124. The coil supporting member 1124 supports the auxiliary coil 1121. In addition, the coil supporting member 1124 is rotatably connected to at least one of the second housing 1123 and the auxiliary coil 1121, and configured to rotate such that a distance between one surface of the second housing 1123 and the auxiliary coil 1121 changes. For example, the coil supporting member 1124 is provided in a form of a cylinder with threads on an outer circumferential surface thereof. When the coil supporting member 1124 rotates, the auxiliary coil 1121 is moved away from or close to one surface of the second housing 1123.

Thus, a user changes a position of the auxiliary coil 1121 in freedom relative to the wireless power transmission apparatus 1110 and a wireless power reception apparatus 1130 by rotating the coil supporting member 1124 or by rotating the first housing 1122 and the second housing 1123. When the auxiliary coil 1121 is disposed by the user at a position at which a transmission coil impedance may be matched, the wireless power transmission apparatus 1110 transmits power to the wireless power reception apparatus 1130 with a minimized loss.

FIG. 12 illustrates an example of matching a transmission coil impedance of a wireless power transmission apparatus and an output impedance.

A wireless power transmission system 1200 provides power to a miniature and ultra-low power electronic device (for example, a wireless power reception apparatus) which is implanted into a living body to provide biomedical stimulation for biometric information sensing or treatment. The wireless power reception apparatus wirelessly receives power from a wireless power transmission apparatus disposed outside of the living body to charge a battery when operating using the battery, or to operate without a battery.

However, when power is directly transmitted from a transmission coil to a reception coil through mutual resonance without using an auxiliary coil, a transmission coil impedance $R_{in}'$ may be mismatched to an output impedance. Such impedance mismatching causes a reflection of power transmitted from a power source to the transmission coil, whereby output power is reduced.

In the example of FIG. 12, the transmission coil impedance $R_{in}'$ measured when an auxiliary coil is absent is modeled as expressed by Equation 1, for example.

$$R_{in}' = R_1 + k_{12}^2 \frac{w_0^2 L_1 L_2'}{R_2' + R_L'} \qquad \text{Equation 1}$$

In Equation 1, $R_1$ and $L_1$ denote a resistance and an inductance of the transmission coil, respectively. $R_2'$ and $L_2'$ denote a resistance and an inductance of the reception coil, respectively. $R_L'$ denotes a resistance of a reception load. $w_0$ denotes a resonance angular velocity of the transmission coil and the reception coil, and is also expressed by $w_0=2\pi f_0$. $f_0$ denotes a resonance frequency. $k_{12}$ denotes a weakly coupling coefficient between the transmission coil and the reception coil. The weakly coupling coefficient is expressed by Equation 2.

$$k_{ij}=f(D_i,D_j,r) \qquad \text{Equation 2:}$$

In Equation 2, $D_i$ denotes a size of an i-th coil, and denotes a size of a j-th coil. r denotes a distance between the two coils. For reference, in FIG. 12, the distance r between the transmission coil and the reception coil is also indicated as a distance d. Thus, $k_{12}$ is determined based on the size $D_1$ of the transmission coil, the size $D_2$ of the reception coil, and the distance d between the transmission coil and the reception coil.

In examples of a wireless power transmission apparatus being implemented as a smart phone, the smart phone may be designed to supply power to a near field communication (NFC) tag of a size of 4 cm to 5 cm at a distance of 2 cm to 3 cm through the air. For example, $L_1=L_2=1.6$ μH, and quality factors of the two coils are $Q_1=Q_2=30$, $R_1=R_2'=w_0L_1/Q_1$, $w_0=2\pi\cdot 13.56$ MHz, $R_L'=R+_2$, and $k_{12}=0.15$. In this example, the transmission coil impedance may be calculated to be 50 ohm. Thus, an impedance matching circuit of the wireless power transmission apparatus is implemented to match the output impedance to a target impedance of 50 ohm. Thus, it is intended that the output impedance of the wireless power transmission apparatus is matched to the target impedance of 50 ohm.

However, unlike the NFC tag device, the wireless power reception apparatus may be implanted into the living body, for example, to a depth of 1 cm, and may include a reception coil of a size of 7 millimeters (mm). Further, $L'_2=40$ nH, and $k_{12}=0.036$ are satisfied. According to Equation 1 provided above, when the size $D_2$ of the reception coil and the distance d change, values of $k_{12}$, $L'_2$, $R'_2$, and $R'_L$ also change, and the value of the transmission coil impedance $R_{in}'$ also changes. Thus, the transmission coil impedance $R_{in}'$ measured when an auxiliary coil is absent decreases to 7 ohm, which leads to a mismatching with the output impedance of 50 ohm of the wireless power transmission apparatus such that power may not be transmitted to the transmission coil due to power reflection.

In a typical wireless power transmission system wherein a variable matching circuit (for example, a circuit using a variable element such as a varactor or a switch) configured to vary and match a transmission coil impedance is introduced as an additional impedance matching circuit, a size of a reception coil and a range of distance covered by the variable matching circuit may be limited, and a manufacturing complexity and a cost for the variable matching circuit may increase.

Unlike the above typical wireless power transmission system, the wireless power transmission system 1200 may matches the transmission coil impedance to the target impedance by disposing an auxiliary coil outside of the living body between the transmission coil disposed outside of the living body and the reception coil disposed inside the living body, as described above with reference to FIGS. 1 through 11, as non-limiting examples. The wireless power transmission system 1200 matches the transmission coil impedance to the target impedance, without using an additional complex variable matching circuit. For example, the transmission coil impedance $R_{in}$ in the wireless power transmission system 1200 including an auxiliary coil is expressed by Equation 3, for example.

$$R_{in} = R_1 + k_{1m}^2 w_0^2 L_1 L_m \left( R_m + k_{m2}^2 \frac{w_0^2 L_m L'_2}{R'_2 + R'_L} \right)^{-1} \quad \text{Equation 3}$$

In Equation 3, $k_{1m}$ denotes a weakly coupling coefficient between the transmission coil and the auxiliary coil, $L_m$ denotes an inductance of the auxiliary coil, $R_m$ denotes a resistance of the auxiliary coil, and $k_{m2}$ denotes a weakly coupling coefficient between the auxiliary coil and the reception coil. The other variables are the same as those described in Equation 1. The transmission coil impedance $R_{in}$ is also determined based on the inductance $L_m$ of the auxiliary coil, the resistance $R_m$ of the auxiliary coil, and the coupling coefficients $k_{1m}$ and $k_{2m}$ between the auxiliary coil and the other coils, in addition to the variables described in Equation 1, as expressed by Equation 3. For reference, the inductance $L_m$ of the auxiliary coil, and the resistance $R_m$ of the auxiliary coil are determined by the size $D_m$ of the auxiliary coil. Further, the coupling coefficients $k_{1m}$ and $k_{2m}$ between the auxiliary coil and the other coils are determined based on the size $D_m$ of the auxiliary coil, the distance g from the transmission coil, and the distance d from the reception coil. Thus, by adjusting the size $D_m$ of the auxiliary coil and the distance g from the transmission coil, the transmission coil impedance $R_{in}$ is matched to a desired target impedance. In Equation 3, the weakly coupling coefficient $k_{12}$ between the transmission coil and the reception coil satisfies $k_{12} \ll k_{1m}$ and $k_{12} \ll k_{m2}$, due to a weak mutual coupling therebetween, and thus is omitted. For example, the weakly coupling coefficient $k_{12}$ between the transmission coil and the reception coil is less than 0.1.

In the example of FIG. 12, the weakly-coupled coupling coefficient between the transmission coil and the auxiliary coil is $k_{1m}=0.15$, and the weakly coupling coefficient between the auxiliary coil and the reception coil is $k_{m2}=0.06$. As described above with reference to FIGS. 1 through 11, by adjusting the size $D_m$ of the auxiliary coil and the distance g, the transmission coil impedance $R_{in}'$ is matched to the target impedance of 50 ohm. Thus, the wireless power transmission apparatus adjusts the variables of the inductance $L_m$ of the auxiliary coil, the resistance $R_m$ of the auxiliary coil, and the coupling coefficients $k_{1m}$ and $k_{2m}$ between the auxiliary coil and the other coils, which are added according to Equation 3, using the auxiliary coil, thereby achieving an optimal transmission coil impedance $R_{in}$.

The wireless power transmission systems, wireless power transmission systems 100 and 1200, wireless power transmission apparatuses, wireless power transmission apparatuses 110, 210, 310, 410, 710, 810, 910, 1010, and 1110, controllers, controller 212, controller 424, communicators, communicator 214, inputters, inputter 215, outputters, outputter 216, auxiliary coil modules, auxiliary coil modules 120, 220, 320, 420, 720, 820, 921, 922, 1020, and 1120, sensors, sensors 322, sensors 422, communicators, communicator 323, communicator 423, wireless power reception apparatuses, wireless power reception apparatuses 130, 230, 430, 730, 830, 930, and 1130 and other apparatuses, units, modules, devices, and other components described herein with respect to FIGS. 1-12 are implemented by or representative of hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 1-12 that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control computing hardware, for example, one or more processors or computers, to implement the hardware components and perform the methods as described above may be written as computer programs, code segments, instructions or any combination thereof, for individually or collectively instructing or configuring the one or more processors or computers to operate as a machine or special-purpose computer to perform the operations that are performed by the hardware components and the methods as described above. In one example, the instructions or software include machine code that is directly executed by the one or more processors or computers, such as machine code produced by a compiler. In another example, the instructions or software includes higher-level code that is executed by the one or more processors or computer using an interpreter. The instructions or software may be written using any programming language based on the block diagrams and the flow charts illustrated in the drawings and the corresponding descriptions used herein, which disclose algorithms for performing the operations that are performed by the hardware components and the methods as described above.

The instructions or software to control computing hardware, for example, one or more processors or computers, to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access programmable read only memory (PROM), electrically erasable programmable read-only memory (EEPROM), random-access memory (RAM), dynamic random access memory (DRAM), static random access memory (SRAM), flash memory, non-volatile memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, blue-ray or optical disk storage, hard disk drive (HDD), solid state drive (SSD), flash memory, a card type memory such as multimedia card micro or a card (for example, secure digital (SD) or extreme digital (XD)), magnetic tapes, floppy disks, magneto-optical data storage devices, optical data storage devices, hard disks, solid-state disks, and any other device that is configured to store the instructions or software and any associated data, data files, and data structures in a non-transitory manner and provide the instructions or software and any associated data, data files, and data structures to one or more processors or computers so that the one or more processors or computers can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A wireless power transmission system, comprising:
a wireless power transmission apparatus comprising:
   a transmission coil configured to form mutual coupling with an auxiliary coil disposed outside of a living body; and
   a controller configured to control a supply of power by a power source to the transmission coil to wirelessly transmit the power from the transmission coil, using the auxiliary coil, to a wireless power reception apparatus disposed inside the living body through the mutual coupling,
   wherein a distance between the transmission coil and the auxiliary coil is adjustable.

2. The system of claim 1, wherein the transmission coil has a structure with a weakly-coupled coupling coefficient less than a threshold value with respect to a reception coil of the wireless power reception apparatus.

3. The system of claim 1, wherein a size of the transmission coil is greater than a size of a reception coil of the wireless power reception apparatus.

4. The system of claim 1, wherein the controller is configured to transmit the power from the power source to the transmission coil, in response to a power transmission input being received from a user.

5. The system of claim 1, further comprising:
a connector configured to:
connect the wireless power transmission apparatus and the auxiliary coil; and
adjust the distance between the transmission coil and the auxiliary coil by adjusting a distance between the wireless power transmission apparatus and the auxiliary coil.

6. The system of claim 5, wherein the connector comprises:
a first housing having one surface configured to be attach to the wireless power transmission apparatus; and
a second housing rotatably connected to the first housing and configured to rotate such that a distance between one surface of the second housing and the one surface of the first housing changes,
wherein the auxiliary coil is disposed parallel with the one surface of the second housing.

7. The system of claim 6, wherein the second housing comprises a coil supporting member supporting the auxiliary coil and rotatably connected to at least one of the second housing and the auxiliary coil, and configured to rotate such that a distance between the one surface of the second housing and the auxiliary coil changes.

8. The system of claim 1, further comprising:
an auxiliary coil module including the auxiliary coil and configured to support the auxiliary coil spaced by a predetermined distance apart from the wireless power transmission apparatus,
wherein the auxiliary coil module is replaceable with another auxiliary coil module with a structure including a differently sized auxiliary coil disposed at a different distance from the wireless power transmission apparatus than the distance between the transmission coil and the auxiliary coil.

9. The system of claim 8, wherein
the wireless power transmission apparatus includes an input/output (I/O) component configured to output either one or both of a replacement indication and a maintenance indication of the auxiliary coil module, and
in response to the auxiliary coil module being replaced with a new auxiliary coil module, the controller is configured to determine whether to replace the new auxiliary coil module based on whether an impedance of the transmission coil reaches a target impedance.

10. The system of claim 1, wherein the auxiliary coil is attached to a surface of the living body.

11. The system of claim 10, wherein the auxiliary coil is replaceable with a differently sized auxiliary coil.

12. The system claim 1, further comprising:
a communicator configured to receive power information related to power of the auxiliary coil from an auxiliary coil module including the auxiliary coil.

13. The system of claim 12, wherein the power information includes information of any one or any combination of any two or more of a voltage, a current, and a magnetic field of the auxiliary coil.

14. The system of claim 12, wherein, based on the received power information, the controller is configured to determine either one or both of whether the distance between the transmission coil and the auxiliary coil is to be adjusted, and whether the auxiliary coil is to be replaced with a differently sized auxiliary coil.

15. The system of claim 12, wherein the controller is configured to output guidance information indicating instructions to either change or maintain the distance between the transmission coil and the auxiliary coil based on the power information.

16. The system of claim 12, wherein
the communicator is configured to collect the power information from the auxiliary coil module at a plurality of distances between the wireless power transmission apparatus and the auxiliary coil, in response to the wireless power transmission apparatus moving in one direction with respect to the auxiliary coil, and
the controller is configured to determine a distance among the plurality of distances at which a maximum magnitude of the collected power information is sensed.

17. The system of claim 16, further comprising:
an input/output (I/O) component configured to output either one or both of an indication to a user that the wireless power transmission apparatus is to be moved in the one direction and an indication to the user that the wireless power transmission apparatus is to be held at the distance at which the maximum magnitude is sensed.

18. The system of claim 1, further comprising:
a communicator configured to transmit, to an auxiliary coil module including auxiliary coils of a plurality of sizes including the auxiliary coil, a signal to activate one of the auxiliary coils.

19. The system of claim 18, wherein
the controller is configured to select the one of the auxiliary coils in the auxiliary coil module based on power information received from the auxiliary coil module, and
for the transmitting of the signal, the communicator is configured to transmit the signal to activate the selected auxiliary coil.

20. The system of claim 18, wherein,
the communicator is configured to transmit signals to sequentially activate the auxiliary coils to the auxiliary coil module, and sequentially receive respective power information corresponding to an activated one of the auxiliary coils sensed by the auxiliary coil module, and
the controller is configured to select, as the one of the auxiliary coils to which the signal to activate is to be transmitted, auxiliary coil of the auxiliary coils corresponding to power information having a maximum magnitude among the sequentially received power information.

21. The system of claim 18, wherein the controller is configured to select, as the one of the auxiliary coils to which the signal to activate is to be transmitted, an auxiliary coil of the auxiliary coils corresponding to a predetermined distance to, and a predetermined size of, a reception coil included in the wireless power reception apparatus.

22. A wireless power transmission method, comprising:
forming, by a transmission coil, mutual coupling with an auxiliary coil disposed outside of a living body; and
controlling a supply of power by a power source to the transmission coil to wirelessly transmit the power from the transmission coil via the auxiliary coil to a wireless power reception apparatus disposed inside the living body through the mutual coupling, wherein a distance between the transmission coil and the auxiliary coil is adjustable.

* * * * *